US005693332A

United States Patent [19]
Hansbrough

[11] Patent Number: 5,693,332
[45] Date of Patent: Dec. 2, 1997

[54] HUMAN KERATINOCYTES SUPPORTED ON A HYDROPHILIC MEMBRANE AND METHODS OF USING SAME TO EFFECT WOUND CLOSURE

[75] Inventor: John F. Hansbrough, Rancho Santa Fe, Calif.

[73] Assignee: The Regents Of The University Of California, Oakland, Calif.

[21] Appl. No.: 513,727

[22] Filed: Aug. 11, 1995

[51] Int. Cl.$^6$ .............................. A61F 2/10; A61F 13/00
[52] U.S. Cl. ..................... 424/426; 424/422; 424/423; 424/424; 424/443; 514/928; 623/15
[58] Field of Search ........................... 424/422, 423, 424/424, 426, 443

[56] References Cited

U.S. PATENT DOCUMENTS 5,326,356  7/1994  Della Valle et al. ............... 623/15

FOREIGN PATENT DOCUMENTS

91/13698  9/1991  WIPO .

OTHER PUBLICATIONS

Barlow, Y.M. et al., "The Use of a Polymeric Film for the Culture and Transfer of Sub-confluent Autologous Keratinocytes to Patients." *J. Tissue Viability*. 2:33–36 (1992).

Hansbrough, John F. et al., "Evaluation of Graftskin★ Compositie Grafts on Full–Thickness Wounds on Athymic Mice." *J. Burn Care & Rehabilitation*. 10 15:346–353 (1994).

Hansbrough, John F. and Cooper, Matthew L., "Methods of Skin Coverage." *Critical Care Report*. 2:48–62 (1990).

Hansbrough, John F. et al., "Development of a Temporary Living Skin Replacement Composed of Human Neonatal Fibroblasts Cultured in Biobrane, a Synthetic Dressing Material." *Surgery*. 115:633–644 (1994).

Hansbrough, John F. et al., "Composite Grafts of Human Keratinocytes Grown on a Polyglactin Mesh–Cultured Fibroblasts Dermal Substitute Function as a Bilayer Skin Replacement in Full–Thickness Wounds on Athymci Mice." *J. Burn Care & Rehabilitation*. 14:485–494 (1993).

*Primary Examiner*—Thurman K. Page
*Assistant Examiner*—James M. Spear
*Attorney, Agent, or Firm*—Campbell & Flores LLP

[57] ABSTRACT

The present invention provides keratinocytes supported on a hydrophilic membrane, the composition being useful as a skin graft to effect closure of a wound. The invention also provides methods of preparing a keratinocyte-containing membrane suitable for effecting wound closure. In addition, the invention provides methods of effecting closure of wound comprising contacting the wound with a keratinocyte-containing membrane.

21 Claims, No Drawings

HUMAN KERATINOCYTES SUPPORTED ON A HYDROPHILIC MEMBRANE AND METHODS OF USING SAME TO EFFECT WOUND CLOSURE

BACKGROUND OF THE INVENTION

1. Field of the Invention

The present invention relates generally to medicine and to wound healing and more specifically to compositions and methods for effecting wound closure.

2. Background Information

Human skin consists of an outer layer of epithelial cells, the epidermis, and an inner layer of supporting tissue, the dermis. The epidermis and dermis are separated by a basement membrane. The skin serves various functions that are vital for survival. For example, the skin is relatively impermeable to water and, therefore, helps prevent undesirable water loss from the body. In addition, the skin acts as a first line of defense for the body against infection. It follows that an injury that wounds the skin can be deleterious to survival and must be quickly and effectively closed.

The epidermis is composed of a continually renewing stratified layer of epithelial cells, called keratinocytes. The basal layer of the epidermis contains epithelial stem cells that divide and give rise to the keratinocytes, which produce keratin as they differentiate and are "pushed" to the surface of the epidermis. As the keratinocytes approach the surface of the epidermis, the cells die and the keratin contributes to the cornified skin surface, which is substantially impermeable to water and acts to prevent bacterial infection. The keratin ultimately is sloughed off from the surface of the skin, but is continually replaced by keratin produced by cells moving from the lower epidermal layers to the surface.

The dermis is a well vascularized tissue that provides support for the epidermis. The dermis contains fibroblasts, which produce various elements of the connective tissue, including the extracellular matrix proteins such as collagens, fibronectin and elastin, which contribute to the strength and flexibility of the skin. Blood vessels present in the dermis transport nutrients to the epithelial cells in the epidermis and carry away waste products of cell metabolism. The basement membrane serves, in part, to attach the epidermis to the dermis. The skin also contains various accessory organs such as hair follicles and sweat glands. Depending on the severity of a wound, any or all of these elements of the skin can be damaged or lost.

An injury to the skin due, for example, to a laceration, a puncture or a burn results in a wound that can extend into or through the skin. If the wound is fairly small and localized, normal healing processes can close the wound and restore normal function to the tissue. In some cases, however, an injury results in a deep wound or a wound that affects a large area. Such wounds can require clinical intervention for healing to occur. For example, a burn that covers a significant portion of the body requires, at a minimum, extensive cleaning of the injured tissue and application of a dressing to prevent infection of the tissue. In addition, skin grafting using undamaged skin from the patient or a skin substitute often is required.

A wound to the skin generally heals by migration of normal epithelial cells from the periphery of the wound into the damaged area. In a minor wound, such reepithelialization may result in complete closure of the wound. Following more serious injuries, however, wound closure may be accompanied by scar formation. If the wound is relatively small, scar formation can be a satisfactory means of repairing the damage. However, where the wound covers an extensive area, scar formation can produce severe disfigurement and loss of function of the injured region.

Use of skin grafting procedures can minimize scarring and reduce the chance of infection of a wound, thus facilitating healing and restoration of normal function of the injured tissue. Ideally, the injured person can provide sufficient undamaged skin from an uninjured part of the body to use for the graft. However, where the injuries are extensive, the availability of donor sites on the patient for grafting are limited, thus delaying permanent coverage of wound.

Mesh grafting and reharvesting of donor sites have been used to avoid a delay in wound closure and increase the rate of permanent closure. However, the use of each of these methods is limited due to potentially deleterious effects. In mesh grafting, slits are mechanically cut in the skin graft, which then is transferred to the wound. The slits allow the skin of the graft to be spread apart, which allows a larger area of the wound to be covered and permits wound fluid to drain through the graft. However, mesh grafting can result in significant scarring that can lead to loss of function of the wounded tissue. Reharvesting of donor skin also is limited in that extensive use of donor sites can result in significant blood loss and patient morbidity. Furthermore, repeated harvesting of skin from the patient requires that the donor site wound be allowed to heal between harvests, thus further delaying the ability of the surgeon to achieve permanent wound closure.

Where the patient cannot provide sufficient amounts of skin for grafting, a number of temporary skin substitutes such as cadaver allograft skin, porcine heterograft, a synthetic material such as Biobrane® (Dow Hickam Inc.; Sugar Land Tex.), which consists of silicone rubber bonded to one surface of a nylon mesh; or a Biobrane®-fibroblast tissue construct have been used. However, while the use of these skin substitutes can be satisfactory as a temporary skin replacement, various complications can occur that necessitate removal of the skin substitute and permanent grafting with the patient's own skin.

An alternative approach to accelerate the availability of graftable tissue has been to obtain a section of undamaged skin from the patient and allow the epithelial cells present in the skin section to grow in tissue culture. Advances in serial subculture techniques of human epithelial cells result in high proliferation rates, which can generate large amounts of epithelium suitable for grafting. The most commonly used culture method involves growing the human epithelial cells in the presence of a "feeder layer" of lethally irradiated mouse fibroblasts, which produce various cellular factors that allow the human cells to form a multistratified epithelium.

Although use of the feeder layer method can produce a sheet of epithelial cells that is suitable for grafting, this method has several limitations. For example, since the cell sheet is grown in culture prior to grafting, it must be physically removed from the culture surface and transferred to the wound. These manipulations require that the sheet be at least four cell layers thick to withstand the trauma of release and transfer. Unfortunately, it can take about three to four weeks to produce a sheet of cells that is suitable for grafting, during which time healing is delayed. In addition, cells of the feeder layer might persist in the graft and can induce an immune and inflammatory response by the patient against the feeder cells. Although methods have been developed to avoid the use of fibroblast feeder layers, they also result in increased cell culture periods to achieve adequate amounts of cultured epithelium.

Even when a cultured sheet of epithelial cells is available for transplant, variable results occur and long term success rates are generally less than 50%. Various factors can account for the low success rate of such grafts. For example, the enzymatic treatment used to remove a newly formed epithelial sheet from a tissue culture plate can alter or destroy cell surface molecules, which, in turn, can alter the ability of the cultured cells to adhere to each other or to the wound. In addition, the multilayered cultured epidermal cells can change from a proliferating state into a differentiated state. However, associated with differentiation of the cells is a loss of expression of certain cell adhesion molecules, which, as indicated above, can alter the binding of the cells to each other and to the wound and, therefore, result in a failure to effect wound closure.

Thus, a need exists for compositions that can effectively and efficiently promote wound closure, methods for making such compositions and methods for using the compositions to effect wound closure. The present invention satisfies this need and provides related advantages as well.

SUMMARY OF THE INVENTION

The present invention provides compositions useful for effecting wound closure, comprising keratinocytes supported on a hydrophilic membrane. A keratinocyte-containing membrane of the invention can contain a subconfluent or confluent monolayer of keratinocytes or can contain multilayered epithelial cells. A hydrophilic membrane containing a subconfluent monolayer of keratinocytes is particularly useful because it can be transferred to a wound after only one or a few days in culture. A composition of the invention is further characterized, in part, in that the hydrophilic membrane is non-toxic and is sufficiently permeable to water such that exudate from a wound does not accumulate. A polyurethane membrane, for example, has such characteristics and provides a suitable support for keratinocytes, allowing their transfer to a wound.

The present invention also provides methods for preparing a keratinocyte-containing membrane suitable for skin grafting by growing keratinocytes, which can be obtained from a patient having a wound, on a hydrophilic membrane, under suitable conditions that allow the cells to proliferate. The invention provides, for example, a method of providing a hydrophilic membrane supported in a tissue culture flask such that a smooth membrane surface is maintained, seeding the membrane with human keratinocytes, and culturing the keratinocyte-seeded membrane for at least one or a few days until a keratinocyte-containing membrane suitable for grafting is obtained.

The invention further provides methods of effecting wound closure in a patient having a wound by contacting the wound with a keratinocyte-containing hydrophilic membrane. A suitable dermal replacement also can be applied to the wound prior to application of the keratinocyte-containing hydrophilic membrane.

DETAILED DESCRIPTION OF THE INVENTION

The present invention provides compositions containing keratinocytes supported on a hydrophilic membrane (HM). A keratinocyte-containing membrane of the invention can contain a subconfluent or confluent monolayer of keratinocytes or can contain multilayered epithelial cells. Preferably, the keratinocytes are present as a subconfluent monolayer of cells on the membrane, which facilitates manipulation of the composition for grafting and provides additional advantages as disclosed herein. A composition of the invention is exemplified by human keratinocytes supported on a hydrophilic polyurethane membrane (see Example I).

A composition of the invention is particularly useful as a skin graft for covering a wound area, thereby effecting wound closure. As used herein, the term "wound" means an injury to the skin that results in damage to or loss of at least a portion of the epidermis. A minor wound, for example, extends through a few layers of the epidermis, whereas a more severe wound can extend into or through the dermis or can cover a relatively large area.

A composition of the invention can be useful for effecting wound closure of a minor wound, particularly if it extends over a significant portion of the body. In general, however, a composition of the invention is useful for effecting closure of a more severe wound. The healing of a deep or extensive wound can result in substantial scarring and loss of function of the injured area. Due to its ability to effect wound closure, a composition of the invention can reduce the amount of scarring and loss of function that otherwise would occur and can minimize the likelihood of bacterial infection.

A composition of the invention also can be useful for effecting the closure of a skin ulcer. As used herein, the term "skin ulcer" means a poorly healing or a non-healing lesion of the skin. Skin ulcers occur, for example, in the extremities of elderly or diabetic patients due to poor circulation and ischemia, or in a patient having a wound in a region that previously was treated by radiation therapy. Ulcers are highly susceptible to bacterial infection and, particularly in diabetics, can result in a need to amputate an affected limb. It should be recognized that a skin ulcer is considered to be within the meaning of the term "wound" as used herein and, therefore, that a composition of the invention is useful for effecting closure of such skin ulcers.

As used herein, the term "wound closure" or "closure" means the process that results in a wound or a portion of a wound becoming covered by a sheet of epithelial cells. Thus, the term "wound closure" is synonymous with "reepithelialization" for purposes of the present invention. The terms "keratinocyte" and "epithelial cell" are used interchangeably herein to mean a cell that produces keratin or gives rise to a cell that produces keratin.

Wound closure can result in the complete coverage of the wound due to the formation of a continuous epithelial cell layer over the injured area. However, even when complete coverage of a wound cannot be attained, significant clinical benefit can result by effecting closure of a portion of the wounded area. In such a case, effecting closure of a portion of the wound can supplement the patient's normal healing response and can reduce the amount of undesirable scarring or loss of function that otherwise would occur.

The compositions of the invention effect wound closure. As used herein, the term "effect" has its commonly understood meaning of "promote." Thus, a keratinocyte-containing membrane of the invention promotes wound closure, thereby facilitating wound healing. For convenience, the term "keratinocyte-containing membrane" is used herein to mean a composition of the invention comprising keratinocytes supported on a hydrophilic membrane. In addition, the term "HK-HM" is used in referring specifically to human keratinocytes (HK) supported on a hydrophilic membrane (HM) and the term "HK-HD" is used in referring to HK supported on the hydrophilic polyurethane membrane, Hydroderm® (HD; see below).

In response to a wound, an acute inflammatory exudate is produced. The exudate is a protein-rich fluid that leaks from the blood vessels present in the injured tissue. Exudate also contains cells, which, along with the proteins present in the exudate, mediate local defense mechanisms at the wound site (see, for example, *Pathology* (ed. Stevens and Lowe; Times Mirror Internatl. Publ., Ltd. 1995); Chapters 5 and 7). In minor wounds, the exudate contributes to healing, then is resolved either by reabsorption or removal from the area. However, the amount of exudate produced generally increases with the area of epithelial cell denudation in the wound area. As a result, in an extensive wound such as a burn, a large amount of exudate can be produced, which, in extreme cases, can lead to dehydration of the patient and shock.

Excision to remove necrotic tissue followed by immediate wound coverage has become the clinical standard in much of the world for managing extensive burn injuries. Wound coverage provides protection of the denuded tissue from bacterial infection, provides an appropriate environment for wound closure and minimizes undesirable fluid loss from the wound area. Where burns are deep or extensive, skin grafting is necessary to effect wound closure and achieve satisfactory healing. In addition to protecting the wound from bacterial infection, keratinocytes present in the graft can provide a source for various growth factors, which can induce migration or proliferation of the keratinocytes, fibroblasts, endothelial cells and neurocytes involved in wound healing, and cytokines, which can regulate the expression or activity of the growth factors (see Myers et al., *Am. J. Surg.* 170:75–83 (1995), which is incorporated herein by reference).

In cases where a patient cannot provide sufficient, undamaged skin for grafting, cell culture technology has made the use of cultured autologous keratinocyte sheets clinically feasible. These methods have focused on developing multilayered, differentiated cell sheets for use as skin grafts. Essentially, a section of undamaged skin is taken from the patient and the epithelial cells are isolated, then cultured until a cell sheet containing about four to six layers of cells forms. The cell sheet then is removed from culture and transplanted to the wound.

Although the use of a cultured multilayered cell sheet as a graft provided a significant advantage over previous methods, the use of a cultured multilayered cell sheet as a graft is limited in several respects. For example, it can take three to four weeks of tissue culture before an adequate cell sheet is formed. In addition, the cell sheets are fragile and, therefore, difficult to manipulate and are susceptible to shrinkage upon removal from culture. Furthermore, the cell sheets must be subjected to enzymatic treatment in order to release the sheet from the tissue culture plate. However, such enzymatic treatment or other treatment to release the cell sheet from the tissue culture plate can alter the characteristics of the cells, causing the cells to lose their adhesive properties. Also, culturing keratinocytes for extended periods of time result in the cells changing from a proliferating stage to a more differentiated state that is associated with a change in the expression of cell surface molecules, which can further affect the adhesive properties of the cells.

A keratinocyte-containing membrane of the invention obviates the problems associated with the use of cultured multilayer epithelial cell sheets. For example, culturing keratinocytes on a HM provides a support for the cells such that handling of the material to be grafted is facilitated. In addition, the use of such a support allows the graft to be transferred to the wound site a short time after the membrane is seeded with the keratinocytes. Specifically, such grafts are suitable for application to a wound about one day to about seven days after seeding, at a time when the cells are not yet confluent. For example, at the seeding density used in the studies of Example I.A., HK-HM were suitable for grafting after about four days in culture. Since the cells are subconfluent when the graft is applied to the wound, the keratinocytes primarily are in the proliferative stage of growth and, therefore, express the appropriate cell surface adhesion molecules (see Example I.B.).

It should be recognized that the invention is particularly useful when a HM contains a subconfluent monolayer of keratinocytes because the keratinocyte-containing membrane can be applied to the wound a short time after the wound is incurred. However, where time allows, the keratinocytes can be cultured to confluency or, if desired, can be grown to form a multilayered epithelial cell sheet of about two to four layers on the HM, which provides a support for the cells and allows their transfer to the wound without the need for enzymatic or other treatment of the keratinocytes.

The present invention provides keratinocytes that are cultured on the surface of a HM. The keratinocyte-containing membrane then is inverted over the wound such that the surface of the keratinocytes that initially was exposed to the medium, i.e., not attached to the HM, ultimately becomes apposed to the wound surface. Thus, the polarity of the keratinocytes must reverse upon their transfer from the culture medium to a wound. Preferably, the keratinocytes are cultured to a subconfluent level or to a confluent monolayer, such that keratinocytes readily can reverse polarity and attach to the wound surface. However, when a multilayered cell sheet is cultured on a HM, then transferred to a wound, the uppermost layer of cells on the membrane ultimately becomes the basal layer of the new epithelium. Consequently, these cells must reverse their polarity so they can attach to the wound surface. The skilled artisan would recognize that the ability of such cells to change their polarity is dependent, for example, on the number of cell layers (see Eaton and Simons, *Cell* 82:5–8 (1995) and references cited therein, each of which is incorporated herein by reference). Thus, the stratified keratinocytes cultured on a HM generally will be limited to about two to four layers prior to transfer to the wound.

Additional aspects of the invention provide further advantages over previously used compositions. For example, HK have been cultured on hydrophobic membranes for transfer to a wound (see Barlow et al., WO 91/13638, 1991; see, also, Barlow et al., *J. Tiss. Viab.* 2:33–36 (1992), each of which is incorporated herein by reference). However, hydrophobic membranes can often require various treatments such as stretching to increase the mesh size or puncturing to assure that an appropriate moisture vapor transmission rate (MVTR) is attained in order to allow adequate evaporation of the liquid component of an exudate. Such treatments, however, compromise the integrity of the membrane, which can render the wound susceptible to bacterial infection.

The MVTR is a measure of the ability of water vapor to traverse a membrane, i.e., its "breathability." Normal skin has an MVTR of about 200–2000 $g/m^2/d$, whereas damaged or burned skin can have a water loss of 3000–5000 $g/m^2/d$ (Lamke et al., *Scand. J. Clin. Lab. Invest.* 37:325–331 (1977); Lamke et al., *Burns* 3:159–165 (1977)). Conventional hydrophobic membranes such as polyether urethane films, which have an equilibrium water content of less than one percent, have an MVTR of about 1500–2000 g/m²/d. However, when coated with a conventional medical adhesive, the MVTR decreases to 500–1000 g/m²/d because the adhesive blocks water vapor transmission. Unfortunately, membranes having a working MVTR less than about 1000 g/m²/d are unsatisfactory for covering medium or high exuding wounds because the exudate rapidly accumulates, leading to maceration of tissue and channeling and leakage, which potentiates infection. Thus, they must be modified by stretching to increase the mesh size or by puncturing the membrane to provide a satisfactory MVTR for use as a wound covering (see Barlow et al., supra, 1990).

As disclosed herein, HK can be cultured on a non-toxic HM such as the hydrophilic polyurethane membrane, Hydroderm® (HD; see Example I). The use of a HM provides an advantage over previously described compositions because the HM can hydrate in the presence of water and, therefore, can better prevent exudate accumulation. The degree of hydration of a hydrophilic membrane depends on the amount of water (exudate) available and is almost 100% reversible. The MVTR of a hydrophilic polymer membrane is dependent upon the degree of hydration such that the MVTR increases as the membrane hydrates and decreases as hydration decreases. This variability in hydration can be useful for maintaining an optimum healing environment by responding to changing conditions of exudate.

A hydrophilic membrane useful in the invention is a non-toxic, biocompatible matrix having certain characteristics that make it particularly suitable as a support for keratinocytes. For example, a HM useful in the invention is characterized, in part, in that it is reversibly hydratable, thus providing an environment that prevents the accumulation of exudate while, at the same time, preventing desiccation of the wound. In addition, a HM useful in the invention has a sufficiently small pore size that reduces or inhibits the ability of bacteria to infect the wound. Various polyurethane membranes as disclosed herein have such characteristics and are commercially available. Furthermore, a HM desirably has the property that it can readily adhere to the wound or can be treated with a bioadhesive, which allows the HM to adhere to the wound without adversely affecting the MVTR of the membrane or the viability of the seeded keratinocytes. A HM useful in the invention also can be biodegradable, which provides the additional advantage that the membrane need not be removed from the healed wound. In addition, a HM can be sufficiently flexible such that it readily conforms to the shape of the body at the wound site.

The hydrophilic polyurethane membrane, Hydroderm® (HD), was selected for use in the studies disclosed herein. HD has been used as a clinical dressing for donor site wounds (Hansbrough et al., *Internatl. Soc. Burn Inj.* (Abstract; 9th Congress; Paris; June 1994)). The MVTR of HD can markedly, but reversibly, increase when it becomes moist. Because of its high, but variable, MVTR, HD can maintain a moist wound surface environment and, at the same time, can control the accumulation of excess fluid exudate. In addition, HD has a biocompatible adhesive coating applied in a criss-cross pattern to one side of the membrane, thus facilitating attachment to the wound area. Furthermore, HD is nontoxic and supports the growth of keratinocytes on its surface.

Other hydrophilic membranes that have characteristics similar to HD or other desirable characteristics such as biodegradability, inherent adhesive properties or conformability also can be used in the present invention as a support for keratinocytes. Such membranes are well known in the art and commercially available. For example, the outer layer film of "MITRAFLEX" (PolyMedica Industries, Inc.; Golden Colo.) is a flexible, transparent polyurethane membrane that allows moisture vapor to be transmitted but is impermeable to other liquids and to microorganisms (see Reed, *J. Biomat. Appl.* 1.6:26–31 (1991), which is incorporated herein by reference). Thus, "MITRAFLEX" is another example of a HM having characteristics that make it suitable for use in the present invention.

Human keratinocytes (HK) were cultured as a subconfluent monolayer on HD membranes using serum-free medium. Such cultured keratinocytes maintained normal expression of cell surface integrins (Example I). When used to cover a full thickness wound in mouse skin, grafting of the HK-containing HD (HK-HD) resulted in markedly improved wound healing as compared to treatment using HD, alone, and resulted in significantly decreased wound contraction (Example II). Thus, a composition of the invention, comprising keratinocytes supported on a hydrophilic membrane, is useful for effecting wound closure and provides a substantial advantage over previously described compositions.

The present invention also provides methods for preparing a keratinocyte-containing membrane suitable for skin grafting by culturing keratinocytes on a hydrophilic membrane. The invention provides, for example, a method of providing a taut HM in a tissue culture vessel, seeding the membrane with human keratinocytes, culturing the keratinocyte-seeded membrane for a suitable period of time such that the cells can proliferate to a desired density, and obtaining a keratinocyte-containing membrane suitable for grafting. Preferably, the keratinocytes are obtained from the patient having the wound to be treated and are cultured on a HM for one or a few days. If desired, a feeder layer of cells also can be present in the tissue culture vessel. If desired, the feeder layer can be situated in the culture vessel such that the feeder layer cells are not in contact with the membrane.

Preferably, the keratinocytes are cultured as a subconfluent monolayer, thus allowing transfer of the keratinocyte-containing membrane to the wound relatively soon after the wound was incurred. As used herein, the term "subconfluent" means a culture that is about 20% to about 95% confluent. In particular, a subconfluent culture is about 50% to about 90% confluent. A subconfluent layer of keratinocytes is characterized, in part, in that the cells primarily are in a proliferating stage of growth. In addition, a subconfluent culture of keratinocytes has not substantially formed multilayered regions and, therefore, have not attained a terminally differentiated state.

In the experiments disclosed herein, human keratinocytes were cultured on HD membranes until a time just prior to their forming a confluent monolayer, then the keratinocyte-containing membrane was removed from culture and used for grafting. Collection of the HK-HD at a time when the cultures have not yet reached confluency allows grafting at a time when the majority of cells are in a proliferating stage and expressing cell surface integrins involved in cell adhesion. The confluency of the cell cultures routinely was monitored by examining the HK-HD using phase contrast microscopy.

For culture, a HM is maintained taut and is submerged in culture medium in order to promote attachment and proliferation of the keratinocytes. As used herein, the term "taut" means that the HM is maintained in a generally flat shape during culture so as to provide a relatively smooth surface for growing the fibroblasts. The definition of the term "taut"

as used herein allows for a moderate amount of slack in the membrane during culture. It should be recognized, however, that the amount of such slack is limited by the formation in the membrane of unacceptable wrinkling, which results in pooling of the seeded keratinocytes into the recesses formed by the wrinkles. Such wrinkling produces an uneven distribution of the seeded keratinocytes on the HM, which can increase the time required for the cells to cover the membrane surface and can reduce the ability of the keratinocyte-containing membrane to conform to a wound. Unacceptable wrinkling can be detected by inspecting the membrane using phase contrast microscopy and identifying pooling of the seeded keratinocytes in the wrinkled regions.

By maintaining a HM taut in the culture vessel, unacceptable wrinkling or shrinkage of the membrane is prevented. The membrane can be maintained sufficiently taut, for example, by suspending it across parallel bars set in a vessel such as a tissue culture flask, by stretching it on a frame, which readily can be placed in the culture vessel, by attaching it directly to the vessel using, for example, a quick setting, water resistant, non-toxic adhesive, or by any other convenient means well known in the art (see, for example, Barlow et al., supra, 1990). The individual components of the vessel, including the culture flask, the HM, the means for maintaining the membrane taut, can be sterilized individually, then assembled under sterile conditions, or can be assembled first, then sterilized.

A suitable number of keratinocytes are seeded on the adhesive surface of the membrane. As used herein in reference to keratinocytes, the term "suitable number" means a number of cells that, when seeded on a HM, form a subconfluent monolayer on the membrane within about one to about seven days. A suitable number of cells generally was about $1 \times 10^4$ to about $1 \times 10^5$ cells per square centimeter of HM. For example, HK-HD suitable for grafting was obtained four days after about $5 \times 10^4$ HK/cm$^2$ HD were seeded on the adhesive-containing side of the membrane (see Example I). It is recognized, however, that the proliferation rate of particular population of keratinocytes can vary markedly among skin samples obtained from different donors depending, for example, on the age of the donor. Thus, a suitable number of keratinocytes for seeding a membrane will depend on the doubling time of the cells as well as on the number of cells available, the size of the membrane to be seeded the culturing conditions. The skilled artisan would know that a suitable number of keratinocytes can be determined empirically using routine tissue culture methods.

If desired, a feeder layer of cells can be provided in the culture to stimulate proliferation of the keratinocytes. A feeder layer of cells can be grown conveniently on the surface of the tissue culture vessel that faces the side of the membrane opposite to the keratinocyte-seeded surface. By culturing the cells in this way, the keratinocytes are maintained separate from the cells of the feeder layer and, upon removal of the membrane from culture, the keratinocyte-containing membrane is substantially free of contaminating feeder layer cells.

Since the keratinocytes are cultured on a hydrophilic membrane, a subconfluent monolayer of cells readily can be removed from the culture chamber and transplanted to the wound surface with minimal manipulation. This ease of achieving transfer of the keratinocytes to the wound within one or a few days after initiating the keratinocyte culture process allows for early treatment of a wound. In contrast, previous methods using multilayered keratinocyte sheets for grafting required waiting three to four weeks until the multilayered cell sheets were formed. Furthermore, the present invention does not require enzymatic or other treatment of the cultured keratinocytes to release them from the culture vessel surface, thus avoiding a tedious and laborious process that can damage the cells and can alter or destroy cell surface proteins such as integrins, which are involved in cell attachment.

A keratinocyte-containing membrane of the invention maintains its shape during culture and upon removal from culture. Thus, the membrane can be cut to the proper dimensions, depending on the size and shape of a wound, prior to placing it in culture and seeding it. As a result, waste of materials and time is minimized. Thus, the present invention provides a substantial advantage over the use of epithelial cell sheets, which markedly contract upon enzymatic release from the surface of a tissue culture vessel, thereby making it difficult to estimate the size of an epithelial sheet that must be cultured in order to cover a particular wound.

A hydrophilic membrane is particularly useful in the present invention if the membrane is a relatively flexible matrix that is easy to manipulate and conforms reasonably well to an irregular wound surface (see, for example, Hansbrough et al., Surgery 115:633–644 (1994)). A HK-HM of the invention is convenient to handle during operative procedures and is easy to move from a tissue culture vessel to a wound. For example, no shrinkage or tearing of the HK-HD occurred during culturing of the cells on the membrane or while transferring or suturing the keratinocyte-containing membrane to a wound (see Examples I and II). In some cases, the markedly convex contour of the mouse flanks, coupled with the constant activity of the mice, caused partial wrinkling of a membrane a few days following application to a wound. However, such wrinkling, which can result in some loss of adherence of cultured HK to the wound surface following transplantation, can be minimized, for example, by adjusting the size of the membrane or by restricting the ability of a patient to move the transplanted site. Alternatively, a HM that is particularly flexible so as to readily conform to an irregular surface can be used as a support for the keratinocytes.

When a cultured multilayer epithelial sheet is used for grafting to a wound, early "take" of a graft is strongly affected by storage and handling of the cultured sheet as well as by the characteristics of the cells forming the sheet (see, for example, Poumay et al., Acta Derma Vene 71:195–198 (1991)). Optimal take of a cultured cell sheet is dependent, in part, on its adhesion to the wound, which is mediated by the integrin family of cell surface receptors. Use of the neutral protease, Dispase (Boehringer-Mannheim; Indianapolis Ind.), to enzymatically detach an epithelial sheet from the surface of a culture vessel provided a marked advantage over the mechanical methods that previously were used for detaching the epithelial sheet. However, Dispase treatment of the cultured epidermal sheets can alter the adhesive properties of the cells in the sheet. For example, $\alpha_6\beta_4$ integrins, which are located in hemidesmisomes and can be involved in epidermal cell/basement membrane adhesion, become internalized in Dispase-detached cultured keratinocytes and, therefore, can become unavailable for adhesion of the cells in the sheet to the wound (Poumay et al., supra, 1993).

In addition, keratinocytes, when cultured to form a multilayered epithelium, change their characteristics from a proliferating state to a more differentiated stage. Associated with differentiation is a change in the expression of adhesion molecules (Hotchin and Watt, J. Biol. Chem.

267:14852–14858 (1992)). For example, differentiated keratinocytes lose the expression of $\alpha_5\beta_1$ integrin (Adams and Watt, Cell 63:425–435 (1990)). Since $\alpha_5\beta_1$ integrin binds to fibronectin, which is a matrix molecule present in high levels in wound tissue, loss of this integrin can alter the ability of the keratinocytes to adhere to the wound. As disclosed herein, however, HK cultured as a subconfluent monolayer on HM remained positive for integrins $\alpha_5$ and $\alpha_6$, which are the major integrins normally expressed on the surface of proliferating HK (Example I). Thus, the present invention provides a keratinocyte-containing membrane suitable for grafting, wherein the keratinocytes express a normal complement of cell adhesion molecules.

The invention further provides methods of effecting wound closure in a patient having a wound by contacting the wound with a keratinocyte-containing hydrophilic membrane. The disclosed methods are particularly useful for effecting closure of an extensive wound covering a significant area of skin or a wound such as a skin ulcer, which is intractable to closure using previously known methods. For example, a wound due to a second or third degree burn can be treated using the present invention. In addition, extensive, deep abrasions that occur, for example, due to an automobile or a motorcycle accident can be treated using the present invention.

As used herein, the term "patient" means a subject having a wound. The present invention is particularly useful for treating human patients such as burn victims. However, the compositions and methods provided herein are readily adaptable to any mammal and, therefore, can be useful for effecting wound closure, for example, in canine, equine, feline or other mammalian "patients."

The efficacy of a composition of the invention for effecting wound closure was demonstrated by treating full thickness wounds in mice. A full thickness wound was made in the flanks of athymic mice, then the wounds were treated with HD, alone, or HK-HD. Histologic analysis performed 21 days after grafting of HD, alone, or HK-HD revealed that reepithelialization of the wounds had occurred in both groups. Examination of the wounds for human involucrin indicated that HK were present in 45.5% of the HK-HD treated wounds but none of the HD treated wounds (Example II). Strong human laminin and human collagen IV immunostaining also was observed in wound areas covered with HK. Remarkably, wound contraction was significantly reduced in mice treated with HK-HD as compared to mice treated with HD, alone.

A suitable dermal replacement also can be applied to the wound prior to application of the keratinocyte-containing hydrophilic membrane. In general, a suitable dermal replacement contains viable fibroblasts seeded on a biodegradable matrix. Suitable biodegradable matrices are well known in the art and include, for example, a collagen-glycosaminoglycan matrix or a polyglactin mesh such as Vicryl mesh (Ethicon, Inc.; Somerville N.J.; see, for example, J. Burn Care Rehab. 13:519–529 (1992)). Fibroblasts obtained from the foreskin of a neonate are particularly useful in a dermal replacement. Upon culture, the fibroblasts can attach to the support and secrete extracellular matrix proteins such as collagen types 1, 3 and 6, elastin, fibronectin and decorin (Hansbrough et al., J. Burn Care Rehab. 14:485–494 (1993), which is incorporated herein by reference). The use of a living dermal replacement provides a suitable environment in the wound for ingrowth of blood capillaries, which can improve the efficiency of graft take and more effectively promote wound closure.

In order to examine the effectiveness of using a dermal replacement in combination with a HK-HM of the invention, the living dermal replacement, Dermagraft® (DG; Advanced Tissue Sciences; La Jolla Calif.), was applied to the wounds of one group of mice, then HK-HD was sutured into place (DG-HK-HD; Example II). DG is a living dermal replacement consisting of neonatal fibroblasts cultured on a biodegradable polyglactin mesh. Similar to the results observed for HK-HD treated wounds, reepithelialization also occurred in DG-HK-HD treated wounds, 50% of the wounds contained cells expressed human involucrin and wound contraction was significantly reduced as compared to treatment with HD, alone. In addition, mice treated with DG-HK-HD developed a thick, well-vascularized neodermis.

The use of effective dermal replacements can improve the capability of achieving functional skin replacements. A functional dermis aids in the development and stability of the epidermis. Reconstitution of the dermal/epidermal junction and, in particular, the basement membrane is necessary to achieve optimal skin strength and durability. As a result, full-thickness wounds that are closed using only a cultured epithelial sheet frequently become fragile and break down; ultrastructural studies demonstrate that wounds closed using cultured epithelial cell sheets lacked critical structures such as anchoring fibrils (see Woodley et al., J. Am. Med. Assoc. 259:2566–2571 (1988)).

The use of Dermagraft® (DG) in combination with HK-HD provided both epidermal and dermal replacement in full-thickness wounds (see Example II). During its culture, the fibroblasts in DG secrete multiple matrix proteins and multiple growth factors (see, for example, Hansbrough et al., J. Burn Care Rehab. 14:485–494 (1993)). As a result, DG can support the adherence and growth of overlaid meshed skin grafts on animals and humans and the growth of cultured keratinocytes in vitro. Since fibroblasts do not appear to be antigenic in the allogeneic situation, DG can;be used as a permanent dermal replacement in humans (see Hansbrough et al., supra, (1992)). In the studies disclosed herein, however, heterologous transplantation of human keratinocytes onto mice would have induced an immune response. Therefore, athymic mice were utilized as graft recipients.

Grafting of proliferating, subconfluent keratinocytes supported on a HM in conjunction with their placement on a living dermal replacement produced wound closure consisting of a multilayered, differentiated epidermis growing on a well-vascularized tissue that resembles dermis (Example II). Strong and continuous staining for laminin and type IV collagen, which are structural proteins present at the dermal/epidermal junction, indicates that the grafts replace important anatomic structures in the full-thickness wound. Wound closure was equally successful in animals receiving HK-HD, alone, or DG-HD-HK. However, staining for specific basement membrane proteins appeared more intense and continuous in the wounds that received DG prior to application of HK-HD.

HD is a useful dressing for covering a clinical wound and effectively controls wound exudates because of its high MVTR. As disclosed herein, HD also can support growth of keratinocytes, thus providing a composition useful for effecting wound closure. Following administration of HK-HD to a wound, keratinocyte proliferation progressed and, after about three weeks, differentiation of the superficial layers of keratinocytes occurred to produce a multistratified and differentiated epidermis. About this time, the HD membrane began to progressively separate and peel away from the reepithelialized wound, leaving behind the newly healed tissue.

The following examples are intended to illustrate but not limit the present invention.

EXAMPLE I

Preparation and Characterization of Keratinocyte-Containing Membranes

This example provides methods for culturing keratinocytes on a hydrophilic polyurethane membrane under conditions that allow the formation of a subconfluent monolayer of cells that are suitable for grafting and methods of characterizing the membrane-bound keratinocytes.

A. Preparation of Keratinocyte-Containing Membranes

Essentially, primary cultures of human keratinocytes were prepared from human skin, then secondary cultures were established on the membrane. Human keratinocytes were isolated from cadaveric donor skin obtained from the University of California San Diego Regional Tissue Bank.

Donor skin was placed overnight at 4° C. in 0.25% trypsin/0.02% EDTA (Gibco/BRL Life Technologies; Grand Island N.Y.). Following incubation of the skin samples, a single cell suspension was prepared and epidermal cells were resuspended and expanded in 75 cm$^2$ polystyrene tissue culture flasks using Keratinocyte-SFM medium (GIBCO). Fourteen days after plating, when the cells had proliferated but had not yet attained confluent growth, the human keratinocytes (HK) were released from the plastic surface with 0.25% trypsin/0.02% EDTA and the cell suspension was adjusted to $2 \times 10^6$ cells/ml.

The synthetic hydrophilic membrane, Hydroderm® (HD; Wilshire Medical Inc.; Dallas Tex.), was used as the support matrix for culturing the keratinocytes. HD is constructed with an adhesive backing formed in a criss-cross pattern on the membrane. When applied to a wound as a dressing, the adhesive side is contacted with the wound, thus holding the dressing in place. In the methods described herein, HK were seeded onto the adhesive side of the HD membrane, which, following culture of the cells, was contacted with the wound.

In initial experiments, a section of HD was placed in a 75 cm$^2$ flask and seeded on its adhesive side with about $5 \times 10^4$ HK per cm$^2$ membrane. However, this attempt to grow cells on HD membrane resulted in marked wrinkling and curling of the HD after several days of submersion in culture medium. This result was not acceptable because it prevented even distribution of the HK on the membrane and would make transplantation of the membrane onto a wound onto a wound difficult.

In order to maintain the HD membrane in a flat shape, a 7×8 cm sterile piece of HD was mounted and stretched flat in a sterile, adjustable polycarbonate frame in the tissue culture flask. This method prevented wrinkling of the membrane and allowed uniform seeding of cells. In order to determine optimal seeding densities of HK, $1 \times 10^4$ to $1 \times 10^5$ HK were seeded per cm$^2$ HD and the membranes were examined daily by phase contrast microscopy. The time at which the HK had proliferated to an appropriate, subconfluent density varied from about 1 to 7 days, depending on the number of HK seeded.

For the experiments disclosed herein, HK were seeded on the adhesive side of the membrane at a density of about $5 \times 10^4$ cells/cm$^2$ HD and fed every 3 days with Keratinocyte-SFM medium. Cell growth was routinely monitored by phase contrast microscopy. HK cells attached to the membrane within about 24 hr and, after about 4–5 days, began to attain confluent growth. At that time, the keratinocyte-containing membrane (HK-HD) was removed and examined as described in Example I.B. or transplanted onto athymic mice (see Example II).

B. Characterization of Keratinocytes Cultured on HD

Upon removal from tissue culture, 1×1 cm sections of HK-HD were mounted onto slides and stained with hematoxylin-eosin using standard methods. Under light microscopy, an HK-HD sample collected 4 days after seeding revealed the presence of multiple HK colonies in almost confluent (subconfluent) coverage of the membrane. No multilayered epidermal areas were observed at this time. Cells attached to and proliferated on the surface of the membrane as well as on the bioadhesive coating, which covers a portion of the membrane surface in a criss-cross pattern.

Integrin expression on HK was examined by immunostaining of cells attached to the HD membrane. The membrane-attached HK were examined for integrin $\alpha_5$ and integrin $\alpha_6$ expression. Integrins were detected on the HK-HD using the Vectastain ABC kit as described by the manufacturer (Vector Laboratories Inc.; Burlingame Calif.). Sections were prepared as described above, then blocked with horse serum, followed by human AB-serum (Sigma Chemical Co.; St. Louis Mo.). Sections were incubated overnight with the 2.5 µg/ml anti-integrin $\alpha_5$ antibody or 2.5 µg/ml anti-integrin $\alpha_6$ antibody (IVF4 or S3–41, respectively; Woods et al., *Arthr. Rheum.* 37:537–544 (1994), which is incorporated herein by reference). The samples then were washed and a biotinylated horse anti-mouse antibody was applied. The samples were washed again, then incubated for 60 min with biotinylated alkaline phosphate H and for 25 min with the substrate alkaline phosphatase substrate kit I (Vector red; Vector Labs).

HK that were cultured on HD demonstrated faint anti-$\alpha_6$ integrin immunoreactivity at the cell borders. Similar staining has been observed in HK grown in tissue culture (see, Marchisio et al., *J. Cell Biol.* 112:761–773 (1991), which is incorporated herein by reference). Integrin $\alpha_6$ staining also was detected on areas of the HD membrane in which HK cells had detached during preparation of the sample for immunohistological analysis. Distinct $\alpha_5$ integrin expression by attached cells also was detected.

Integrin expression of enzymatically detached HK grown in tissue culture was determined using flow cytometry. HK were cultured in plastic tissue culture flasks until just reaching confluent growth, then enzymatically detached from the flask using 4 U/ml Dispase (Boehringer-Mannheim) or 0.25% trypsin. The detached HK were prepared for flow cytometry and analyzed on a FACStar flow cytometer (Becton Dickinson; San Jose Calif.; see Woods et al., *Arthr. Rheum.* 37:537–544 (1994), which is incorporated herein by reference).

For integrin labeling, $1 \times 10^5$ HK were washed in 50 µl staining buffer (Hank's balanced saline solution containing 0.02% sodium azide), then incubated with the integrin-specific mouse antibodies described above (IVF4 for $\alpha_5$ or S3–41 for $\alpha_6$, 20 µg/ml) for 1 hr, washed, and stained with fluorescein isothiocyanate-conjugated anti-mouse IgG antibody (Caltag Laboratories; South San Francisco Calif.). Cells then were washed and incubated with propidium iodide prior to flow cytometry. Viable keratinocytes were gated by cell size and propidium iodide exclusion. The percentage of integrin-positive trypsin-detached keratinocytes (3 separate experiments) was compared with that of Dispase-detached cells by gating the cells over secondary antibody stained cells.

Flow cytometry analysis revealed strong expression of the integrin $\alpha_5$ on confluent, single-layer keratinocytes. No significant differences were observed in comparing Dispase-detached HK with trypsin-detached HK. In contrast, integrin $\alpha_6$ expression was significantly reduced (p=0.039) on Dispase-detached HK (74.3+0.36%) as compared to trypsin-detached HK (91.07+3.69%). These results demonstrate that Dispase treatment, which is routinely used to effectively remove cultured epithelial sheets from plastic surfaces prior to their transplantation to a wound, alters or destroys the expression of integrin $\alpha_6$ that is otherwise present on the surface of proliferating keratinocytes.

EXAMPLE II

Use of HK-HD Grafts to Effect Wound Closure

This example demonstrates that human keratinocyte-containing Hydroderm® (HK-HD) is useful for effecting closure of a full thickness wound in mouse skin.

Athymic mice (Balb/c-nu/nu;, 4–8 weeks old; Simonsen Laboratories; Gilroy Calif.) were housed in isolation rooms. Surgery and dressing changes were performed in laminar flow hoods. Prior to surgery, mice were anesthetized by intraperitoneal (ip) injection of 10 mg Avertin (Aldrich Chemical Inc.; Milwaukee Wis.) in 0.4 ml normal saline. The dorsolateral surface of the mouse was washed with povidone-iodine and 70% isopropanol. Full thickness skin defects were created by excising a 2×2 cm section of skin (dermis and epidermis), but sparing the panniculus carnosis. The grafts were then sutured over the defect with 6-0 silk.

Experiments were performed using three different treatment groups. In the first group (n=4), the defect was covered with Hydroderm®, alone (i.e., HD not containing HK). For this group, the HD membrane was maintained in Keratinocyte-SFM medium for at least 24 hr prior to the surgery. In the second group (n=11), the defect was covered with HK-HD prepared as described in Example I.A. In the third group (n=14), a 2×2 cm section of Dermagraft® (DG; Advanced Tissue Sciences Inc.; LaJolla Calif.) was sutured into the defect, then covered with HK-HD (DG-HK-HD). All grafts were covered with a bulky gauze dressing to compress and stabilize the grafts and the animals were wrapped circumferentially with a self-adherent Band-Aid® bandage (Johnson and Johnson; New Brunswick N.J.) to protect the treated sites from mechanical disturbance.

Animals were administered daily ip injections of 3 mg ceftazidime (Glaxo, Inc.; Research Triangle Park; N.C.) for 7 days after surgery. Sulfamethoxazole and trimethoprim were administered by addition to autoclaved drinking water (200 mg sulfamethoxazole/40 mg trimethoprim in 200 ml water; Biocraft Laboratories; Elmwood Park N.J.). The mortality rate of the grafting procedure was approximately 5%. Animals were examined for the integrity of dressings each day postoperatively during the entire study, then were sacrificed on day 21 after grafting and the wounds were examined histologically and immunohistochemically.

1. Gross Examination

HD, alone, or containing HK, adhered to the wound bed within 2 days of grafting. Beginning about 17 days after grafting, the HD membrane began to peel from the wounded area. Wounds were closed in all groups after about 17 to 21 days and a silvery pink appearance of the wound surface was present. The silvery pink appearance preceded the spontaneous separation of the HD membrane from the healing epithelium.

On day 21 after grafting, the mice were killed and the wounds were photographed. The wound areas then were excised down through the dorsal muscle bed for histologic evaluation. A circumferential rim of murine skin was harvested with the wound. Wound contraction was observed but was not quantified. Severe wound contraction (approximately 90% contraction by day 21) occurred in wounds covered with HD, alone. In contrast, only moderate contraction occurred in the wounds covered by HK-HD or with DG-HK-HD (approximately 50% contraction by day 21). The wounds of animals that received DG prior to HK-HD coverage generally contracted less than the wounds of animals that did not receive DG. These results demonstrate that HK-HD effects wound closure and reduces the amount of undesirable wound contraction that otherwise would occur.

2. Histologic Examination

For routine light microscopy, tissue samples obtained from mice sacrificed at day 21 after grafting were fixed in 10% formalin, embedded in paraffin, sectioned at 5 µm thickness, mounted onto slides and stained with hematoxylin-eosin. Wounds that were covered with HD, alone, showed only a small area of reepithelialization. In contrast, animals that received HK-HD in a single operative procedure showed a continuous multilayer epidermis overlying a thick, defined neodermis having a high amount of vascularity. In the DG-HK-HD animals, the excised wound revealed the presence of a stratified layer of epidermal cells resting on a thin layer of connective tissue covering skeletal muscle. In comparison to HK-HD treated mice, a thick layer of well-vascularized neodermal tissue, which contained large numbers of fibroblasts and many blood vessels, formed in the DG-HK-HD treated mice.

3. Immunohistochemical Examination

Immunohistochemical staining was utilized to identify the presence of human-specific proteins in the treated wounds. Human involucrin in healed wounds on the athymic mice was determined using the Histostain-SP Kit as described by the manufacturer (Zymed Laboratories Inc.; San Francisco Calif.). Frozen sections were fixed, rehydrated and treated with 10% non-immune goat serum to block nonspecific binding. Slides were incubated with rabbit anti-human involucrin antibody (Biomedical Technologies, Inc.; Stoughton Mass.) for 60 min, then rinsed. Following incubation with the primary antibody, the sample was incubated for 10 min with biotinylated goat anti-rabbit antibody, then rinsed. Enzyme conjugate then was applied for 10 min, the sample was rinsed and the slides were incubated 10 min in the Substrate-Chromogen Mixture (3-amino-9-ethylcarbazole; AEC). Positive staining appeared as a red precipitate in the superficial epidermal layer.

Immunohistochemical staining for human involucrin revealed that human keratinocytes were present and persisted in the murine wounds treated with HK-HD or DG-HK-HD. 45.5% of the animals treated with HK-HD and 50% of the animals treated with DG-HK-HD contained HK, as determined by positive staining for human involucrin. In these HK positive wounds, up to about 50% of the reepithelialized length of the wound was covered by HK; the remainder of the wound was reepithelialized by murine keratinocytes, which had migrated from the wound margins. Wounds treated with HD, alone, were negative for human involucrin staining. In the DG-HK-HD treated mice, the areas of human skin were characterized by a well-defined multilayered epidermis and contained a thick, well-vascularized neodermis.

Immunohistochemical analysis for human collagen type IV or human laminin was performed using 7 µm frozen sections, which were prepared as described above. Samples were incubated with rabbit anti-human collagen IV or rabbit anti-human laminin I (Chemicon; Temecula Calif.), then washed, incubated with a biotinylated secondary antibody, washed again and incubated with enzyme conjugate and AEC as described above.

Human collagen type IV and human laminin were detected at the dermal-epidermal junction in mice treated with HK-HD or DG-HK-HD (see Table); no staining for either human collagen type IV or human laminin was detected in wounds closed with HD, alone. Although not quantitated, a more continuous expression of basement membrane antigens appeared to be present in animals that received DG-HK-HD. These results demonstrate that keratinocytes can be cultured on a hydrophilic membrane and used to effect closure of a wound.

Although the invention has been described with reference to the examples provided above, it should be understood that various modifications can be made without departing from the spirit of the invention. Accordingly, the invention is limited only by the claims.

I claim:

1. A composition for effecting wound closure, comprising keratinocytes supported on a hydrophilic membrane, wherein said membrane has a sufficiently small pore size that reduces or inhibits the ability of bacteria to infect the wound.

2. The composition of claim 1, wherein said keratinocytes are human keratinocytes.

3. The composition of claim 1, wherein said membrane is a polyurethane membrane.

4. A method of effecting wound closure in a patient having a wound, comprising contacting the wound with keratinocytes supported on a hydrophilic membrane, wherein said membrane has a sufficiently small pore size that reduces or inhibits the ability of bacteria to infect the wound.

5. The method of claim 4, wherein said wound is a burn.

6. The composition of claim 1, wherein said keratinocytes comprise a subconfluent monolayer of said keratinocytes.

7. The composition of claim 1, wherein said keratinocytes comprise a confluent monolayer of said keratinocytes.

8. The composition of claim 1, wherein said keratinocytes comprise a multilayered cell sheet of said keratinocytes.

9. A method of obtaining a composition for effecting wound closure, comprising keratinocytes supported on a hydrophilic membrane, comprising the steps of:

a. tautly mounting the hydrophilic membrane in a vessel wherein said membrane has a sufficiently small pore size that reduces or inhibits the ability of bacteria to infect the wound;

b. seeding said membrane with a suitable number of the keratinocytes;

c. thereafter, incubating said keratinocyte-seeded membrane under conditions that allow proliferation of said keratinocytes; and d. terminating said incubating step, wherein said keratinocytes supported on said membrane is obtained.

10. The method of claim 9, wherein said suitable number is between about 10,000 and about 100,000 keratinocytes per square centimeter of said membrane.

11. The method of claim 9, wherein said membrane is a polyurethane membrane.

12. The method of claim 4, wherein said wound is a skin ulcer.

13. The method of claim 4, wherein said keratinocytes comprise a subconfluent monolayer of said keratinocytes.

14. The method of claim 9, further comprising seeding said vessel with a feeder layer of cells.

15. The method of claim 9, wherein said keratinocytes supported on a hydrophilic membrane comprise a subconfluent monolayer of said keratinocytes.

16. The method of claim 9, wherein said keratinocytes supported on a hydrophilic membrane comprise a confluent monolayer of said keratinocytes.

17. The method of claim 9, wherein said keratinocytes supported on a hydrophilic membrane comprise a multilayered cell sheet of said keratinocytes.

18. The method of claim 4, wherein said patient is a human patient.

19. The method of claim 4, wherein said membrane is a polyurethane membrane.

20. The method of claim 4, wherein said keratinocytes comprise a confluent monolayer of said keratinocytes.

21. The method of claim 4, wherein said keratinocytes comprise a multilayered cell sheet of said keratinocytes.

* * * * *

(12) REEXAMINATION CERTIFICATE (4251st)
United States Patent
Hansbrough

(10) Number: US 5,693,332 C1
(45) Certificate Issued: Jan. 9, 2001

(54) HUMAN KERATINOCYTES SUPPORTED ON A HYDROPHILIC MEMBRANE AND METHODS OF USING SAME TO EFFECT WOUND CLOSURE

(75) Inventor: John F. Hansbrough, Rancho Santa Fe, CA (US)

(73) Assignee: The Regents of the University of California, Oakland, CA (US)

Reexamination Request:
No. 90/005,055, Aug. 5, 1998

Reexamination Certificate for:
Patent No.: 5,693,332
Issued: Dec. 2, 1997
Appl. No.: 08/513,727
Filed: Aug. 11, 1995

(51) Int. Cl.⁷ .............................. A61F 2/10; A61F 13/00
(52) U.S. Cl. ..................... 424/426; 424/422; 424/423; 424/424; 424/443; 514/928
(58) Field of Search ...................... 424/422, 423, 424/424, 426, 443; 514/928; 623/15

(56) References Cited

U.S. PATENT DOCUMENTS

| | | | |
|---|---|---|---|
| 5,326,356 | 7/1994 | Della Valle et al. | 623/15 |
| 5,395,305 | 3/1995 | Kolde et al. | 602/48 |
| 5,445,604 | 8/1995 | Lang | 602/47 |
| 5,460,939 | * 10/1995 | Hansbrough | 435/1.1 |

OTHER PUBLICATIONS

G.J. Beumer et al., Advances in Biomaterials, 9:169–174 (1990).

L. Andreassi et al., Wounds, 3(3):116–126 (1991).

S. Gogolewski et al., Makromol. Chem., Rapid Commun., 4:675–680 (1983).

M.F. Jonkman et al., Journal of Biomaterials Applications, 5(1):3–19 (1990).

* cited by examiner

*Primary Examiner*—James M. Spear

(57) ABSTRACT

The present invention provides keratinocytes supported on a hydrophilic membrane, the composition being useful as a skin graft to effect closure of a wound. The invention also provides methods of preparing a keratinocyte-containing membrane suitable for effecting wound closure. In addition, the invention provides methods of effecting closure of wound comprising contacting the wound with a keratinocyte-containing membrane.

REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

The patentability of claims 9–11 and 14–17 is confirmed.

Claims 1–5, 18 and 19 are cancelled.

Claims 6–8, 12, 13, 20 and 21 are determined to be patentable as amended.

New claimes 22–24 are added and determined to be patentable.

6. [The composition of claim 1,] *A composition for effecting wound closure, comprising keratinocytes supported on a hydrophilic membrane, wherein said membrane has a sufficiently small pore size that reduces or inhibits the ability of bacteria to infect the wound,* wherein said keratinocytes comprise a subconfluent monolayer of said keratinocytes.

7. [The composition of claim 1,] *A composition for effecting wound closure, comprising keratinocytes supported on a hydrophilic membrane, wherein said membrane has a sufficiently small pore size that reduces or inhibits the ability of bacteria to infect the wound,* wherein said keratinocytes comprise a confluent monolayer of said keratinocytes.

8. [The composition of claim 1,] *A composition for effecting wound closure, comprising keratinocytes supported on a hydrophilic membrane, wherein said membrane has a sufficiently small pore size that reduces or inhibits the ability of bacteria to infect the wound,* wherein said keratinocytes comprise a multilayered cell sheet of said keratinocytes.

12. [The method of claim 4,] *A method of effecting wound closure in a patient having a wound, comprising contacting the wound with keratinocytes supported on a hydrophilic membrane, wherein said membrane has a sufficiently small pore size that reduces or inhibits the ability of bacteria to infect the wound,* wherein said wound is a skin ulcer, *and wherein the keratinocytes are in a configuration selected from the group consisting of a subconfluent monolayer, a confluent monolayer and a multilayered cell sheet.*

13. [The method of claim 4,] *A method of effecting wound closure in a patient having a wound, comprising contacting the wound with keratinocytes supported on a hydrophilic membrane, wherein said membrane has a sufficiently small pore size that reduces or inhibits the ability of bacteria to infect the wound,* wherein said keratinocytes comprise a subconfluent monolayer of said keratinocytes.

20. [The method of claim 4, ] *A method of effecting would closure in a patient having a wound, comprising contacting the wound with keratinocytes supported on a hydrophilic membrane, wherein said membrane has a sufficiently small pore size that reduces or inhibits the ability of bacteria to infect the wound,* wherein said keratinocytes comprise a confluent monolayer of said keratinocytes.

21. [The method of claim 4,] *A method of effecting wound closure in a patient having a wound, comprising contacting the wound with keratinocytes supported on a hydrophilic membrane, wherein said membrane has a sufficiently small pore size that reduces or inhibits the ability of bacteria to infect the wound,* wherein said keratinocytes comprise a multilayered cell sheet of said keratinocytes.

*22. The method of claim 12, wherein the keratinocytes are in a subconfluent monolayer.*

*23. The method of claim 12, wherein the keratinocytes are in a confluent monolayer.*

*24. The method of claim 12, wherein the keratinocytes are in a multilayered cell sheet.*

* * * * *